United States Patent
Okita

(10) Patent No.: US 9,675,239 B2
(45) Date of Patent: Jun. 13, 2017

(54) ENDOSCOPE SYSTEM

(71) Applicant: OLYMPUS CORPORATION, Tokyo (JP)

(72) Inventor: Yoshinari Okita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/134,825

(22) Filed: Apr. 21, 2016

(65) Prior Publication Data

US 2016/0227993 A1 Aug. 11, 2016

Related U.S. Application Data

(63) Continuation of application No. PCT/JP2014/073951, filed on Sep. 10, 2014.

(30) Foreign Application Priority Data

Jan. 9, 2014 (JP) .................................. 2014-002612

(51) Int. Cl.
*A61B 1/06* (2006.01)
*A61B 1/00* (2006.01)
(Continued)

(52) U.S. Cl.
CPC ............ *A61B 1/07* (2013.01); *A61B 1/00006* (2013.01); *A61B 1/00009* (2013.01);
(Continued)

(58) Field of Classification Search
CPC ..... A61B 1/07; A61B 1/0669; A61B 1/00006; A61B 1/00096; A61B 1/0646; A61B 1/0009
See application file for complete search history.

(56) References Cited

U.S. PATENT DOCUMENTS

| 4,569,334 A | 2/1986 | Ohshiro |
| 4,953,937 A | 9/1990 | Kikuchi et al. |
| 2012/0289779 A1 | 11/2012 | Kinoshita et al. |

FOREIGN PATENT DOCUMENTS

| EP | 0067555 A2 | 12/1982 |
| EP | 2520213 A1 | 11/2012 |

(Continued)

OTHER PUBLICATIONS

International Search Report dated Dec. 9, 2014 issued in PCT/JP2014/073951.

(Continued)

*Primary Examiner* — Timothy J Neal
(74) *Attorney, Agent, or Firm* — Scully, Scott, Murphy & Presser, P.C.

(57) ABSTRACT

An endoscope system includes: an insertion portion insertable into a body cavity of a subject; an illumination fiber guiding light caused to be incident on a proximal-end-side end face, to a distal-end-side end face; a light-receiving fiber group guiding light from the subject and emitting the light; a light source portion generating illuminating light; a light detecting portion; a first optical unit capable of changing an optical path of the illuminating light caused to be incident on the proximal-end-side end face of the illumination fiber; a second optical unit capable of changing the optical path for the illuminating light changed by the first optical unit and causing the illuminating light to be incident on the light-receiving fiber group; and a control portion performing control of whether or not to change the optical path in the first optical unit and the second optical unit.

4 Claims, 12 Drawing Sheets

(51) Int. Cl.
*A61B 1/07* (2006.01)
*A61B 1/04* (2006.01)
(52) U.S. Cl.
CPC ...... *A61B 1/00045* (2013.01); *A61B 1/00096* (2013.01); *A61B 1/00165* (2013.01); *A61B 1/00172* (2013.01); *A61B 1/042* (2013.01); *A61B 1/0646* (2013.01); *A61B 1/0669* (2013.01)

(56) References Cited

FOREIGN PATENT DOCUMENTS

| | | |
|---|---|---|
| JP | S57-192533 A | 11/1982 |
| JP | S57-192534 A | 11/1982 |
| JP | S57-192536 A | 11/1982 |
| JP | S58-73332 A | 5/1983 |
| JP | S58-172602 A | 10/1983 |
| JP | S61-134722 A | 6/1986 |
| JP | H02-114226 A | 4/1990 |
| JP | 2007-014633 A | 1/2007 |
| WO | WO 2012/050116 A1 | 4/2012 |

OTHER PUBLICATIONS

Japanese Office Action dated Aug. 25, 2015 issued in JP 2015-525336.

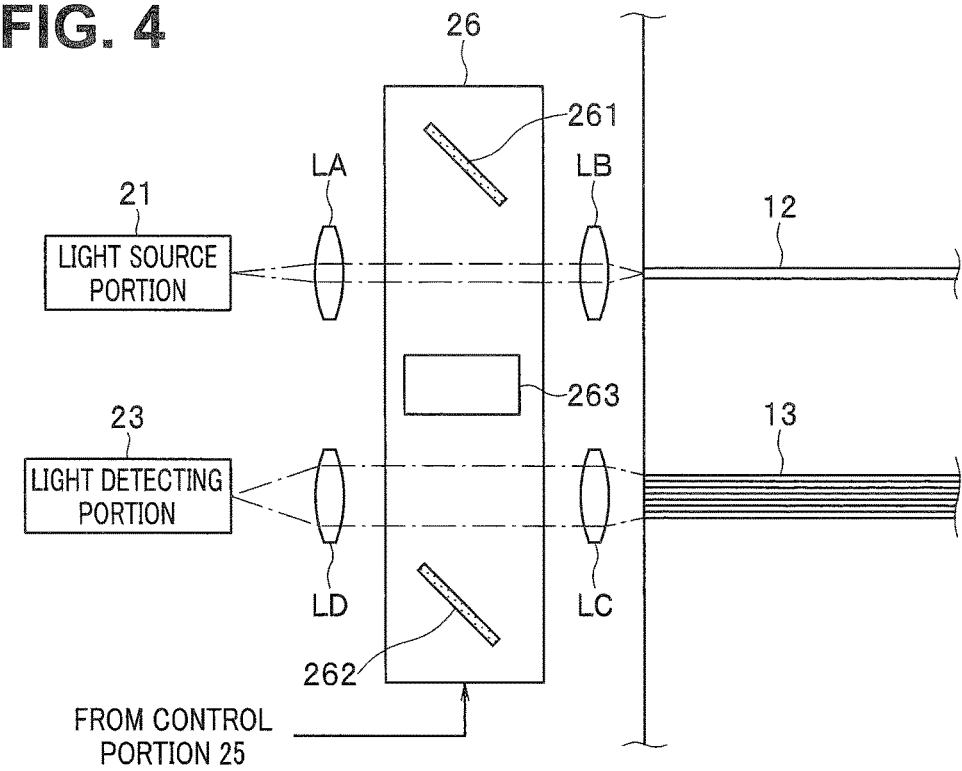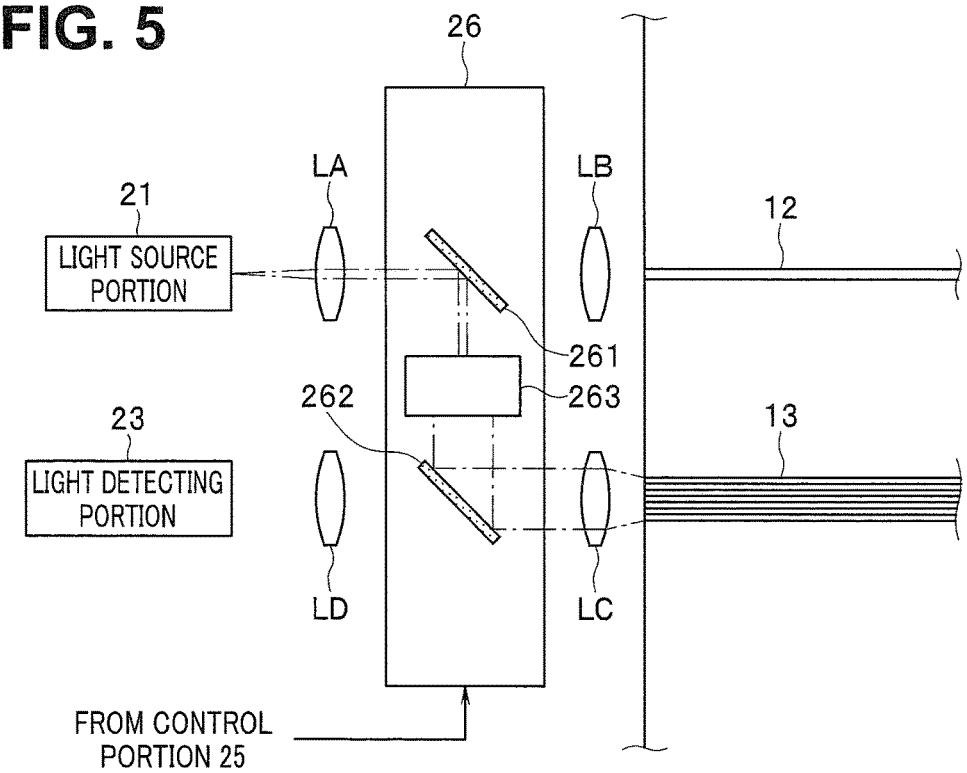

ENDOSCOPE SYSTEM

CROSS REFERENCE TO RELATED APPLICATION

This application is a continuation application of PCT/JP2014/073951 filed on Sep. 10, 2014 and claims benefit of Japanese Application No. 2014-002612 filed in Japan on Jan. 9, 2014, the entire contents of which are incorporated herein by this reference.

BACKGROUND OF THE INVENTION

1. Field of the Invention

The present invention relates to an endoscope system, and in particular to an endoscope system which scans an object to acquire an image.

2. Description of the Related Art

For endoscopes in a medical field, various techniques for reducing a diameter of an insertion portion inserted into a body cavity of a subject have been proposed in order to reduce a burden on the subject. As an example of such techniques, a scanning-type endoscope which does not have a solid image pickup device in a portion corresponding to the insertion portion described above, and a system configured being provided with the scanning-type endoscope are known.

More specifically, the system provided with the scanning-type endoscope is configured, for example, to two-dimensionally scan an object in a preset scan pattern by swinging a distal end portion of a light guiding fiber which guides light emitted from a light source portion, receive return light from the object by a light-receiving fiber and generate an image of the object based on the return light received by the light-receiving fiber.

On the other hand, among optical fibers, there are, for example, some provided with such an optical characteristic that transmittance is reduced at time of being exposed to a radiation such as an X ray and that recovery of the reduction of the transmittance is accelerated by adding light having a relatively high intensity.

For example, Japanese Patent Application Laid-Open Publication No. S58-73332 discloses a technique for accelerating recovery of transmittance of an optical fiber which has been reduced by exposure to a radiation.

More specifically, Japanese Patent Application Laid-Open Publication No. S58-73332 discloses such a configuration that, in an endoscope, a transmittance of an optical glass fiber bundle for image transmission is recovered close to an initial transmittance (at time of manufacture) by providing a predetermined optical device (prism or mirror) for deflecting light emitted from a light emission end face of an optical fiber bundle for light transmission in an insertion portion and arranging the predetermined optical device at a position where the emitted light is caused to be incident on an image incident surface of the optical glass fiber bundle for image transmission.

SUMMARY OF THE INVENTION

An endoscope system of an aspect of the present invention includes: an elongated insertion portion insertable into a body cavity of a subject; an illumination fiber provided outside the insertion portion, the illumination fiber guiding light caused to be incident on a proximal-end-side end face of the insertion portion to a distal-end-side end face of the insertion portion; a light-receiving fiber group provided in the insertion portion, the light-receiving fiber group guiding light from the object caused to be incident on the distal-end-side end face of the insertion portion and emitting the light from the proximal-end-side end face of the insertion portion; a light source portion generating illuminating light for illuminating an object in the body cavity of the subject, the light source being arranged at a position where the illuminating light is caused to be incident on a proximal-end-side end face of the illumination fiber; a light detecting section arranged at a position where the light from the object emitted from the light-receiving fiber group is caused to be incident; a first optical unit arranged on an optical path of the illuminating light generated by the light source portion, the first optical unit being capable of changing the optical path of the illuminating light caused to be incident on the proximal-end-side end face of the illumination fiber; a second optical unit arranged on an optical path from the end face of the light-receiving fiber group from which the light from the object is emitted to the light detecting portion, the second optical unit being capable of changing the optical path of the illuminating light changed by the first optical unit to cause the illuminating light to be incident on the end face of the light-receiving fiber group from which the light from the object is emitted; and a control portion performing control of whether or not to change the optical path in the first optical unit and the second optical unit.

BRIEF DESCRIPTION OF THE DRAWINGS

FIG. 4 is a diagram showing an example of an operation state of the optical unit according to the first embodiment;

FIG. 5 is a diagram showing an example of the operation state of the optical unit according to the first embodiment different from the example in FIG. 4;

DETAILED DESCRIPTION OF THE PREFERRED EMBODIMENTS

Embodiments of the present invention will be described below with reference to drawings.

First Embodiment

Figure 1:
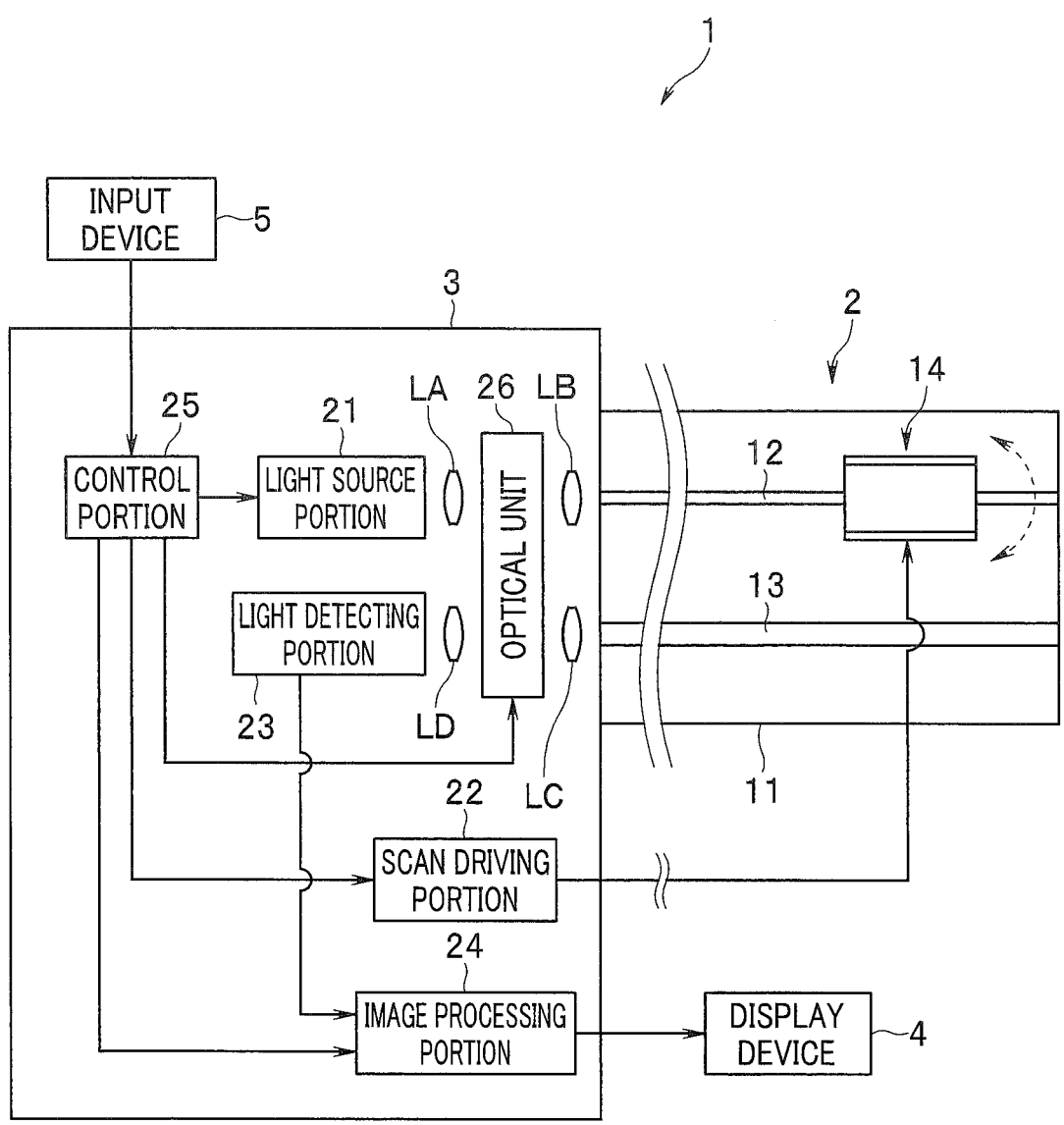
FIG. 1 is a diagram showing a configuration of main portions of an endoscope system according to a first embodiment.

FIGS. 1 to 5 relate to a first embodiment of the present invention. FIG. 1 is a diagram showing a configuration of main portions of an endoscope system according to the first embodiment.

An endoscope system 1 is configured, for example, having a scanning-type endoscope 2 insertable into a body cavity of a subject, a body apparatus 3 to which the scanning-type endoscope 2 can be connected, a display device 4 capable of displaying an observed image and the like outputted from the body apparatus 3, and an input device 5 capable of inputting information and giving an instruction to the body apparatus 3, as shown in FIG. 1. Note that the input device 5 is not limited to such that is configured as a device different from the body apparatus 3 as shown in FIG. 1 but may be configured as an interface integrated with the body apparatus 3.

The scanning-type endoscope 2 can be inserted into a body cavity of a subject and has an insertion portion 11 formed in an elongated cylindrical shape.

A connector portion (not shown) for detachably connecting the scanning-type endoscope 2 to a connector receiving portion (not shown) of the body apparatus 3 is provided at a proximal end portion of the insertion portion 11.

In a part from the proximal end portion to a distal end portion inside the insertion portion 11, each of an illumination fiber 12 and a light-receiving fiber group 13 is inserted.

The illumination fiber 12 is formed, for example, as an optical fiber which includes glass and the like, and is configured to be capable of guiding illuminating light supplied from the body apparatus 3 and emitting the guided illuminating light from a distal-end-side end face (arranged at the distal end portion of the insertion portion 11) (an emission-end-side end face) to an object.

The light-receiving fiber group 13 is configured, for example, with a plurality of optical fibers bundled which include glass and the like, and configured to be capable of receiving return light of illuminating light emitted from the illumination fiber 12 to an object (reflected light generated by the illuminating light emitted from the illumination fiber 12 being reflected by the object) by a distal-end-side end face (an incident-end-side end face) and guiding the return light to the body apparatus 3. Further, the light-receiving fiber group 13 is configured to be capable of guiding light supplied from the body apparatus 3 in order to accelerate recovery of transmittance.

An actuator portion 14 which is configured to swing an end portion including the distal-end-side end face (an emission-end-side end portion) of the illumination fiber 12 in response to a drive signal supplied from the body apparatus 3 is provided inside the insertion portion 11.

Figure 2:
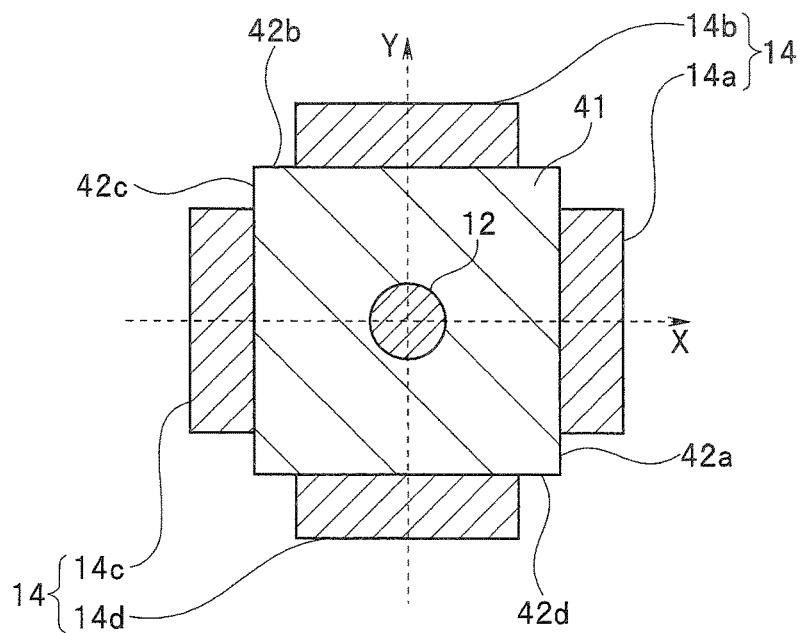
FIG. 2 is a cross-sectional view for illustrating a configuration of an actuator portion provided in a scanning-type endoscope.

On the other hand, each of the illumination fiber 12 and the actuator portion 14 is arranged, for example, so that a positional relationship shown in FIG. 2 is provided on a section vertical to a longitudinal axis direction of the scanning-type endoscope 2. FIG. 2 is a cross-sectional view for illustrating the configuration of the actuator portion provided in the scanning-type endoscope.

As shown in FIG. 2, a ferrule 41 as a joining member is arranged between the illumination fiber 12 and the actuator portion 14.

More specifically, the ferrule 41 is formed, for example, with zirconia (ceramic) or nickel.

The ferrule 41 is formed as a quadrangular prism as shown in FIG. 2 and has side faces 42a and 42c vertical to an X axis direction (a right/left direction on the paper) and side faces 42b and 42d vertical to a Y axis direction (an upward/downward direction on the paper). Further, the illumination fiber 12 is fixed and arranged at a center of the ferrule 41. Note that the ferrule 41 may be formed in a shape other than the quadrangular prism.

As shown in FIG. 2, the actuator portion 14 has an actuator 14a arranged along the side face 42a, an actuator 14b arranged along the side face 42b, an actuator 14c arranged along the side face 42c and an actuator 14d arranged along the side face 42d.

The actuators 14a and 14c are formed, for example, by piezoelectric elements and configured to be capable of swinging the end portion of the illumination fiber 12 which includes the distal-end-side end face along the X axis direction by being driven (expanding and contracting) in response to a drive signal supplied from the body apparatus 3.

The actuators 14b and 14d are formed, for example, by piezoelectric elements and configured to be capable of swinging the end portion of the illumination fiber 12 which includes the distal-end-side end face along the Y axis direction by being driven (expanding and contracting) in response to a drive signal supplied from the body apparatus 3.

On the other hand, the body apparatus 3 is configured having a light source portion 21, a scan driving portion 22, a light detecting portion 23, an image processing portion 24, a control portion 25, an optical unit 26, a lens LA provided near a light emission port (not shown) of the light source portion 21, a lens LB provided near a proximal-end-side end face (an incident-end-side end face) of the illumination fiber 12, a lens LC near a proximal-end-side end face (an emission-end-side end face) of the light-receiving fiber group 13 and a lens LD provided near a light incident port (not shown) of the light detecting portion 23 as shown in FIG. 1.

The light source portion 21 is configured to be capable of supplying (emitting from the light emission port) illuminating light for illuminating an object in a body cavity of a subject into which the insertion portion 11 is inserted.

More specifically, for example, the light source portion 21 is provided with a laser light source for R light which emits R light, which is light in a red color gamut, a laser light source for G light which emits G light, which is light in a green color gamut, and a laser light source for B light which emits B light, which is light in a blue color gamut so as to supply white light (RGB light) obtained by combining lights emitted from the respective laser light sources as illuminating light.

Further, the light source portion 21 is configured, for example, to be capable of starting or stopping supply of illuminating light by switching between on and off states of each laser light source in response to control of the control portion 25.

The scan driving portion 22 is, for example, provided with a drive circuit and the like and is configured to supply a drive signal for causing the actuator portion 14 to be driven, based on control of the control portion 25.

The light detecting portion 23 is, for example, provided with a demultiplexer, an optical sensor and the like and is configured to separate return light caused to be incident (from the light incident port) into R (red), G (green) and B (blue) color components, generate color signals corresponding to lights separated according to the color components and output the color signals to the image processing portion 24.

The image processing portion 24 is configured to be able to generate an observed image corresponding to color signals outputted from the light detecting portion 23 and outputting the observed image to the display device 4 based on control of the control portion 25. Further, the image processing portion 24 is configured to be capable of generating visual information such as character strings according to control of the control portion 25 and outputting the generated visual information to the display device 4.

The control portion 25 is provided with a CPU and the like and is configured to be capable of performing various controls based on a control program read from a memory not shown.

More specifically, the control portion 25 is configured, for example, to perform control for causing the end portion of the illumination fiber 12 which includes the distal-end-side end face to swing (along the predetermined track) so that an illumination position of illuminating light emitted from the insertion portion 11 draws a predetermined track, for the scan driving portion 22 based on the control program read from the memory not shown.

Further, the control portion 25 is configured to be capable of performing various controls based on operations performed on the input device 5.

More specifically, the control portion 25 is configured, for example, to perform control related to acceleration of recovery of transmittance of the light-receiving fiber group 13 when detecting that a predetermined switch SW (not shown) of the input device 5 is on. Note that details of such control will be described later.

Figure 3:
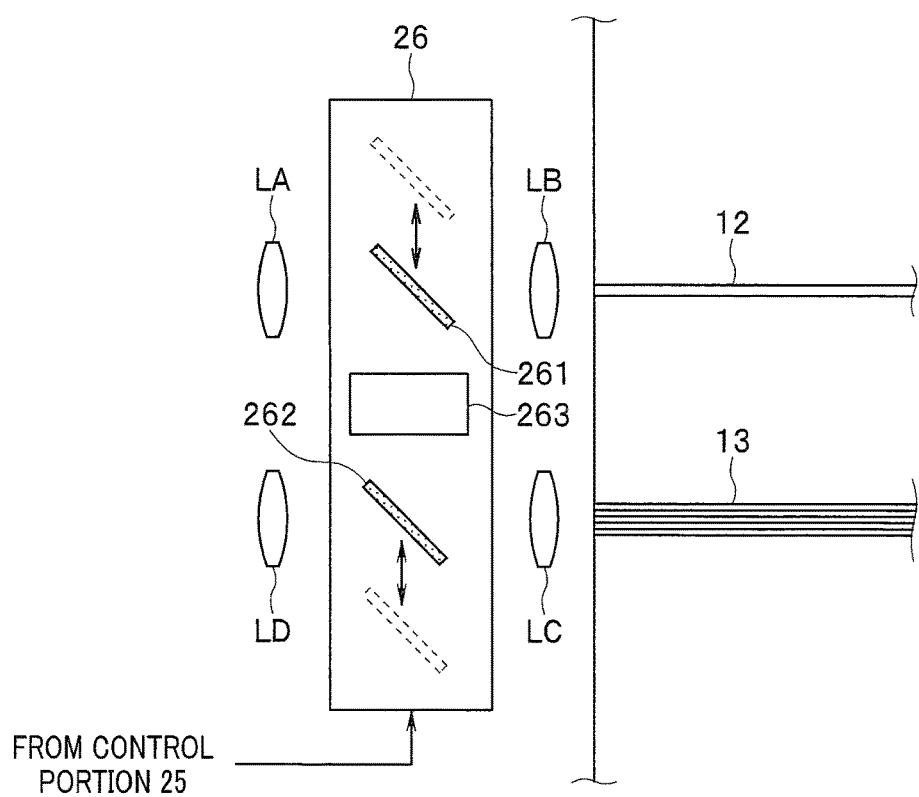
FIG. 3 is a diagram for illustrating an example of a configuration of an optical unit according to the first embodiment.

As shown in FIG. 3, the optical unit 26 is arranged so as to be located midway on an optical path of illuminating light emitted via the lens LA from the light source portion 21 and located midway on an optical path of return light emitted via lens LC from the proximal-end-side end face of the light-receiving fiber group 13. Further, the optical unit 26 is configured, for example, having movable mirrors 261 and 262, and a luminous flux diameter changing portion 263 as shown in FIG. 3. FIG. 3 is a diagram for illustrating an example of the configuration of the optical unit according to the first embodiment.

The movable mirror 261 is configured, for example, to move to a position where the movable mirror 261 can reflect illuminating light emitted via the lens LA to a luminous flux diameter changing portion 263 side (a predetermined position on an optical path from the lens LA to the lens LB) when the predetermined switch SW of the input device 5 is on, in response to control of the control portion 25. Further, the movable mirror 261 is configured, for example, to be capable of moving to a position where the movable mirror 261 can cause the illuminating light emitted via the lens LA to be transmitted to a lens LB side (a predetermined position outside the optical path from the lens LA to the lens LB) when the predetermined switch SW of the input device 5 is off, in response to control of the control portion 25.

The movable mirror 262 is configured, for example, to move to a position where the movable mirror 262 can reflect illuminating light emitted via the luminous flux diameter changing portion 263 to a lens LC side (a predetermined position on an optical path from the lens LC to the lens LD) when the predetermined switch SW of the input device 5 is on, in response to control of the control portion 25. Further, the movable mirror 262 is configured, for example, to be capable of moving to a position where the movable mirror 262 can cause the illuminating light emitted via the lens LC to be transmitted to a lens LD side (a predetermined position outside the optical path from the lens LC to the lens LD) when the predetermined switch SW of the input device 5 is off, in response to control of the control portion 25.

The luminous flux diameter changing portion 263 is arranged at a predetermined position on an optical path from the movable mirror 261 to the movable mirror 262. Further, the luminous flux diameter changing portion 263 is provided, for example, with a beam expander and is configured to change a luminous flux diameter of illuminating light caused to be incident via the movable mirror 261 when the predetermined switch SW is on so that the luminous flux diameter becomes a size matching a bundle diameter of the light-receiving fiber group 13 (expand the luminous flux diameter so that the luminous flux diameter becomes a same or substantially same size as the bundle diameter of the light-receiving fiber group 13) and emit the illuminating light to a movable mirror 262 side.

That is, the optical unit 26 can perform a switching operation for causing illuminating light emitted via the lens LA from the light source portion 21 to be incident either on the incident-end-side end face of the illumination fiber 12 or on the emission-end-side end face of the light-receiving fiber group 13 by moving the movable mirrors 261 and 262 in response to control of the control portion 25.

The lens LA is configured, for example, being provided with an optical characteristic of emitting illuminating light supplied from the light source portion 21 as parallel light.

The lens LB is configured, for example, being provided with an optical characteristic of condensing illuminating light (parallel light) emitted via the lens LA and the optical unit 26 and causing the illuminating light to be incident on the proximal-end-side end face of the illumination fiber 12.

The lens LC is configured, for example, being provided with an optical characteristic of emitting return light emitted from the proximal-end-side end face of the light-receiving fiber group 13 as parallel light, and condensing illuminating light emitted via the optical unit 26 and causing the illuminating light to be incident on the proximal-end-side end face of the light-receiving fiber group 13.

The lens LD is configured, for example, being provided with an optical characteristic of condensing return light (parallel light) emitted via the lens LC and the optical unit 26 and causing the return light to be incident on the light detecting portion 23.

Next, an operation of the endoscope system 1 according to the present embodiment will be described.

A user such as a surgeon makes an instruction for starting supply of illuminating light by operating the input device 5 in a state that the predetermined switch SW of the input device 5 is off, after connecting each portion of the endoscope system 1 and turning on power.

The control portion 25 performs control for causing supply of illuminating light to be started, for the light source portion 21 based on the instruction made on the input device 5. Further, when detecting that the predetermined switch SW of the input device 5 is off, the control portion 25 performs control, for example, for causing the movable mirrors 261 and 262 of the optical unit 26 to move to positions as shown in FIG. 4. FIG. 4 is a diagram showing an example of an operation state of the optical unit according to the first embodiment.

Then, by the control of the control portion 25 as described above, illuminating light emitted from the light source portion 21 when the predetermined switch SW is off is caused to be incident on the proximal-end-side end face of the illumination fiber 12 after being transmitted through the lens LA and the lens LB sequentially. Then, by the control of the control portion 25 as described above, return light emitted from the proximal-end-side end face of the light-receiving fiber group 13 when the predetermined switch SW is off is caused to be incident on the light detecting portion 23 after being transmitted through the lens LC and the lens LD sequentially.

On the other hand, the user performs an operation for switching the predetermined switch SW of the input device 5 from off to on after confirming that illuminating light is being emitted from the insertion portion 11.

When detecting that the predetermined switch SW of the input device 5 is on, the control portion 25 performs control, for example, for causing the movable mirrors 261 and 262 of the optical unit 26 to move to positions as shown in FIG. 5. FIG. 5 is a diagram showing an example of an operation state of the optical unit according to the first embodiment, which is different from the example in FIG. 4.

Then, by the control of the control portion 25 as described above, illuminating light emitted from the light source portion 21 when the predetermined switch SW is on is caused to be incident on the proximal-end-side end face of the light-receiving fiber group 13 after being transmitted through the lens LA, the movable mirror 261, the luminous flux diameter changing portion 263, the movable mirror 262 and the lens LC sequentially.

As described above, by the endoscope system 1 according to the present embodiment, it is possible to accelerate recovery of transmittance of the light-receiving fiber group 13 without providing a dedicated optical member and the like in the insertion portion 11. Therefore, according to the present embodiment, it is possible to accelerate recovery of transmittance of a light-receiving fiber without uselessly increasing a diameter of an insertion portion.

Note that it is possible to, by appropriately modifying the configuration and the like described above, apply the present embodiment not only to the case where the light-receiving fiber group 13 is configured being provided with a plurality of optical fibers but also to a case where the light-receiving fiber group 13 is configured being provided with one optical fiber.

Second Embodiment

FIGS. 6 to 13 relate to a second embodiment of the present invention.

Figure 6:
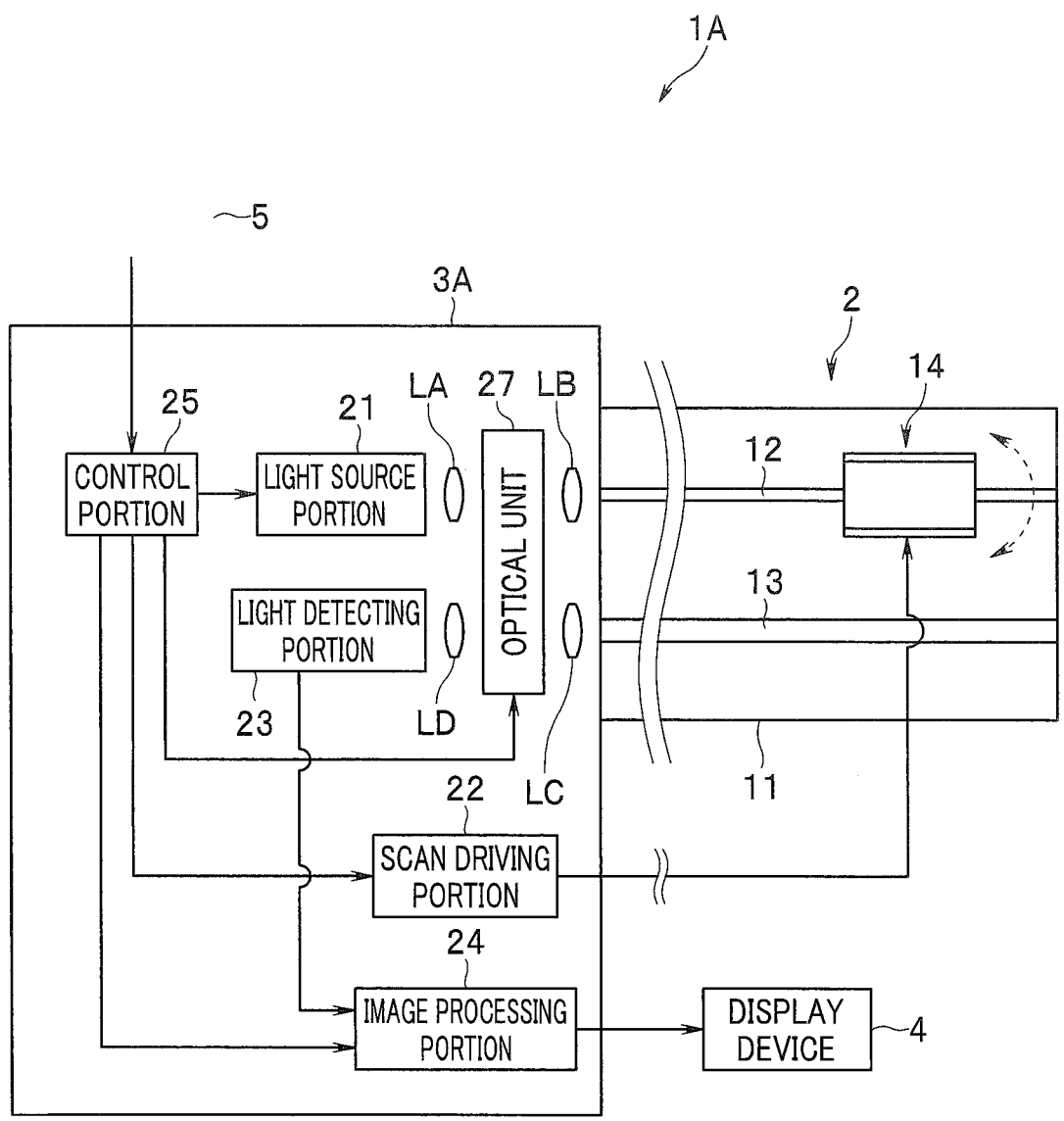
FIG. 6 is a diagram showing a configuration of main portions of an endoscope system according to a second embodiment.

Note that, in the present embodiment, detailed description on parts having configurations and the like similar to those of the first embodiment will be omitted, and description will be made mainly on parts having configurations and the like different from those of the first embodiment. FIG. 6 is a diagram showing a configuration of main portions of an endoscope system according to the second embodiment.

An endoscope system 1A is configured, for example, having a body apparatus 3A instead of the body apparatus 3 in the endoscope system 1, as shown in FIG. 6. Further, the body apparatus 3A is configured having an optical unit 27 instead of the optical unit 26 in the body apparatus 3.

Figure 7:
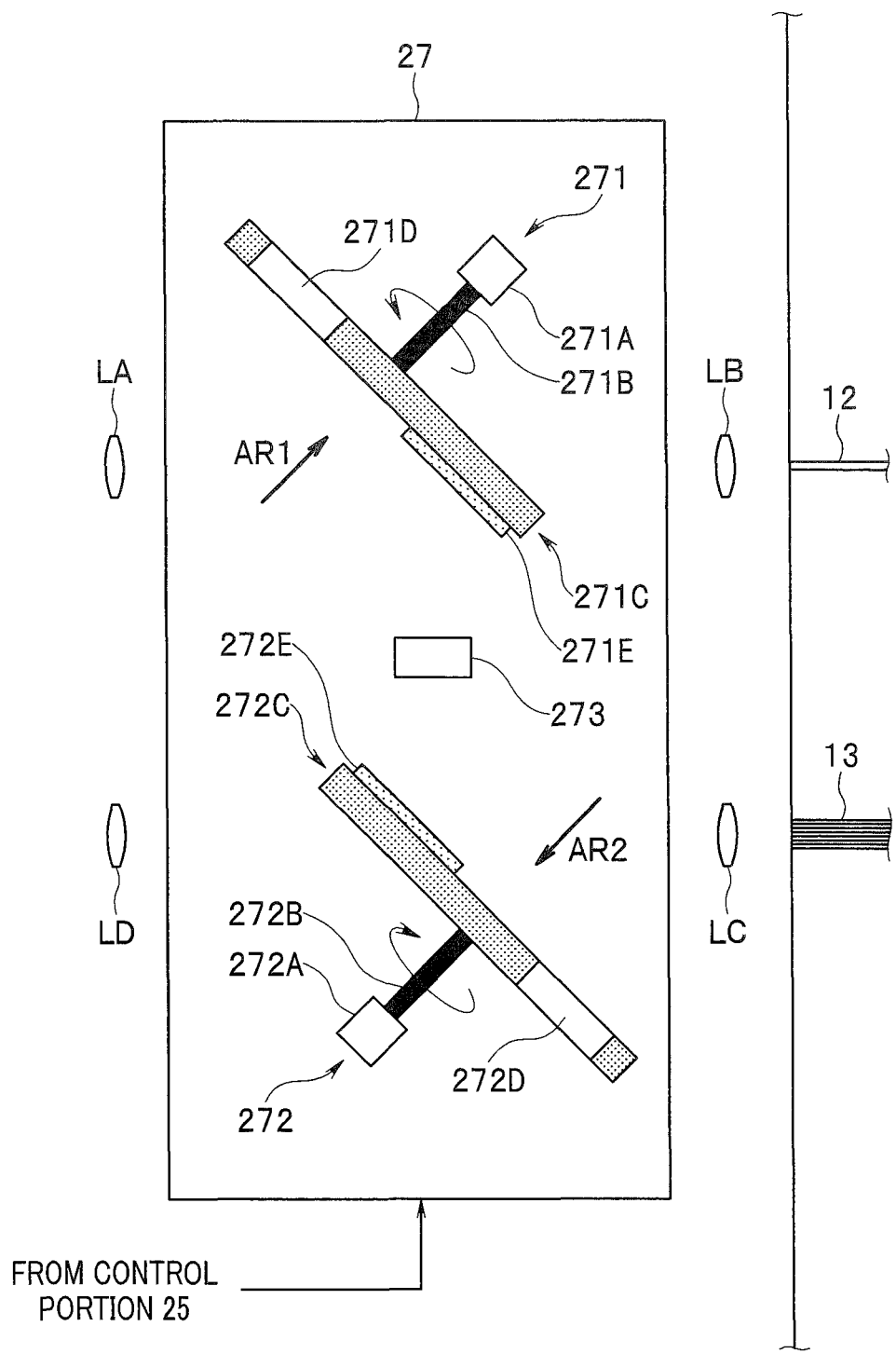
FIG. 7 is a diagram for illustrating an example of a configuration of an optical unit according to the second embodiment.

The optical unit 27 is configured, for example, having rotating mirror mechanisms 271 and 272, and a luminous flux diameter changing portion 273 as shown in FIG. 7. FIG. 7 is a diagram for illustrating an example of a configuration of the optical unit according to the second embodiment.

The rotating mirror mechanism 271 is configured, for example, having a motor 271A which rotates in response to control of the control portion 25, a rotating shaft 271B which transmits rotation force generated by rotation of the motor 271A, a rotating plate 271C configured such that an end portion of the rotating shaft 271B is provided at a central part, as shown in FIG. 7.

The rotating plate 271C is formed, for example, being provided with a disk shape and is configured to rotate in conjunction with rotation of the rotating shaft 271B. Further, the rotating plate 271C is arranged so as to obliquely cross the optical path of illuminating light emitted via the lens LA (for example, so as to form an acute angle relative to the optical path of the illuminating light emitted via the lens LA). Furthermore, the rotating plate 271C is configured having an opening portion 271D and a mirror 271E.

Figure 8:
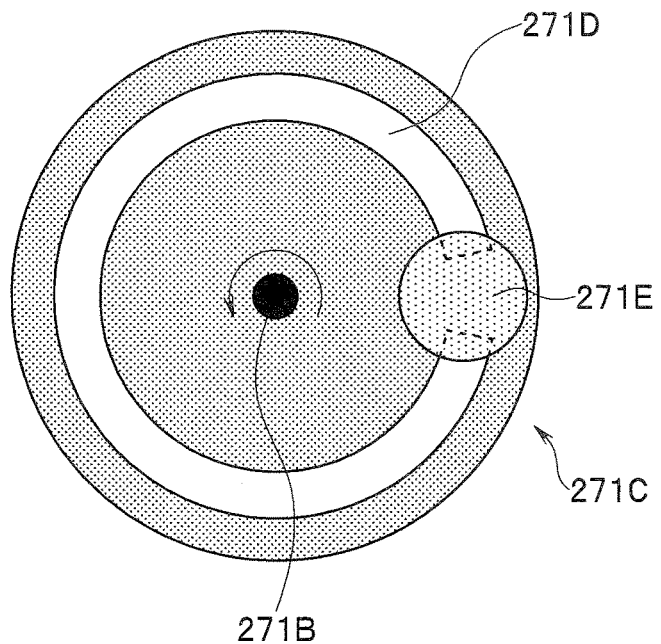
FIG. 8 is a diagram showing an example of a configuration of a rotating plate when the rotating plate is seen from a direction indicated by an arrow AR1 in FIG. 7.

The opening portion 271D is formed, for example, being provided with a C shape (an arc shape) as shown in FIG. 8 when seen from a direction indicated by an arrow AR1 in FIG. 7 and configured to cause illuminating light emitted via the lens LA to be transmitted. FIG. 8 is a diagram showing an example of a configuration of the rotating plate when seen from the direction indicated by the arrow AR1 in FIG. 7. Note that, according to the present embodiment, for example, a transparent member capable of transmitting illuminating light emitted via the lens LA may be provided at the opening portion 271D.

The mirror 271E is formed, for example, being provided with such a shape (a disk shape) that covers both end portions of the C-shaped opening portion 271 D and is arranged at a position where the mirror 271E can reflect illuminating light emitted via the lens LA to a luminous flux diameter changing portion 273 side, as shown in FIG. 8.

The rotating mirror mechanism 272 is configured, for example, having a motor 272A which rotates in response to control of the control portion 25, a rotating shaft 272B which transmits rotation force generated by rotation of the motor 272A, a rotating plate 272C configured such that an end portion of the rotating shaft 272B is provided at a central part, as shown in FIG. 7.

The rotating plate 272C is formed, for example, being provided with a disk shape and is configured to rotate in conjunction with rotation of the rotating shaft 272B. Further, the rotating plate 272C is arranged so as to obliquely cross the optical path of return light emitted via the lens LC (for example, so as to form an obtuse angle relative to the optical path of the return light emitted via the lens LC). Furthermore, the rotating plate 272C is configured having an opening portion 272D and a mirror 272E, as shown in FIG. 7.

Figure 9:
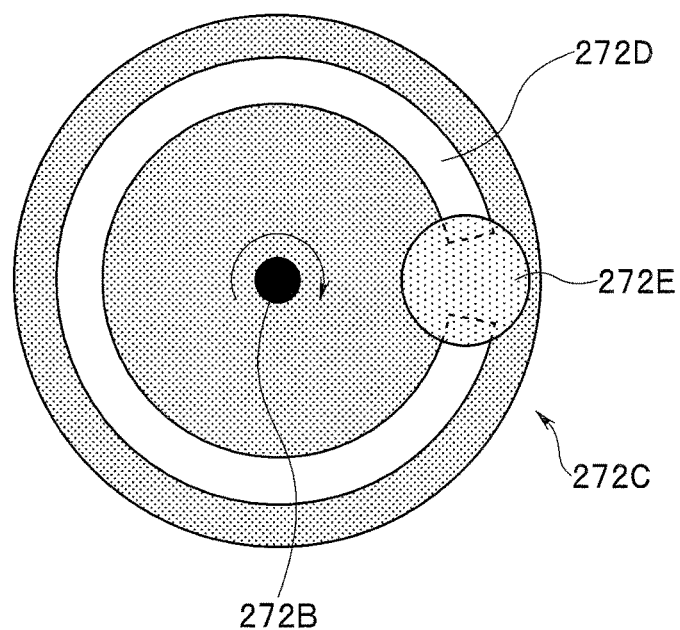
FIG. 9 is a diagram showing an example of a configuration of a rotating plate when the rotating plate is seen from a direction indicated by an arrow AR2 in FIG. 7.

The opening portion 272D is formed, for example, being provided with a C shape (an arc shape) as shown in FIG. 9 when seen from a direction indicated by an arrow AR2 in FIG. 7 and configured to cause return light emitted via the lens LC to be transmitted. FIG. 9 is a diagram showing an example of the configuration of the rotating plate when seen from the direction indicated by the arrow AR2 in FIG. 7. Note that, according to the present embodiment, for example, a transparent member capable of transmitting return light emitted via the lens LC may be provided at the opening portion 271D.

The mirror 272E is formed, for example, being provided with such a shape (a disk shape) that covers both end portions of the C-shaped opening portion 272D and is arranged at a position where the mirror 272E can reflect illuminating light emitted via the luminous flux diameter changing portion 273 to a lens LC side, as shown in FIG. 9.

The luminous flux diameter changing portion 273 is arranged on an optical path LP from the mirror 271E to the mirror 272E, which is an optical path temporarily formed accompanying rotation of the rotating plates 271C and 272C. Further, the luminous flux diameter changing portion 273 is provided, for example, with a beam expander and is configured to change a luminous flux diameter of illuminating light caused to be incident via the mirror 271E when the optical path LP is formed so that the luminous flux diameter becomes a size matching the bundle diameter of the light-receiving fiber group 13 (for example, expand the luminous flux diameter so that the luminous flux diameter becomes a same or substantially same size as the bundle diameter of the light-receiving fiber group 13) and emit the illuminating light to a mirror 272E side.

That is, the optical unit 27 can perform a switching operation for causing illuminating light emitted via the lens LA from the light source portion 21 to be incident either on the incident-end-side end face of the illumination fiber 12 or on the emission-end-side end face of the light-receiving fiber group 13 by rotating the motors 271A and 272A in response to control of the control portion 25.

On the other hand, the control portion 25 of the present embodiment is configured to perform control for causing the optical path LP to be formed during a period until a predetermined time period elapses after scanning for acquiring observed images corresponding to a predetermined number of frames is performed. Note that, details of such control will be described later.

Next, an operation of the endoscope system 1A according to the present embodiment will be described.

The user makes an instruction for causing acquisition of an observed image by the scanning-type endoscope 2 and the body apparatus 3A to be started, by operating the input device 5 after connecting each portion of the endoscope system 1A and turning on power.

When detecting that the instruction for causing acquisition of an observed image by the scanning-type endoscope 2 and the body apparatus 3A to be started has been made, the control portion 25 performs control for causing supply of illuminating light to be started, for the light source portion 21, and performs control for causing the end portion of the illumination fiber 12 which includes the distal-end-side end face to swing so that an illumination position of illuminating light emitted from the insertion portion 11 draws a spiral-shaped track, for the scan driving portion 22. Further, while causing the end portion of the illumination fiber 12 which includes the distal-end-side end face to swing, the control portion 25 performs control for causing illuminating light supplied from the light source portion 21 to be incident on the proximal-end-side end face of the illumination fiber 12 and also causing return light emitted from the proximal-end-side end face of the light-receiving fiber group 13 to be incident on the light detecting portion 23, for the optical unit 27.

Figure 10:
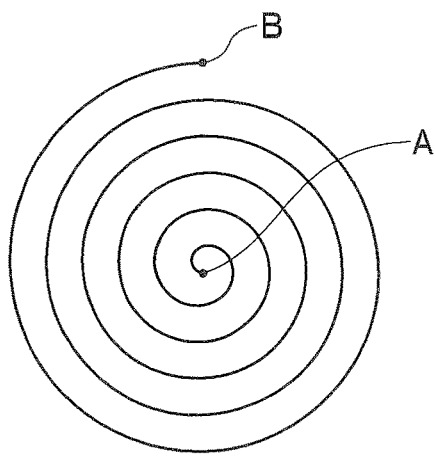
FIG. 10 is a diagram showing an example of a case where, in a scan for acquiring an observed image of an object, the scan is performed so as to advance from a center point A of a spiral-shaped track to an outermost point B.
Figure 11:
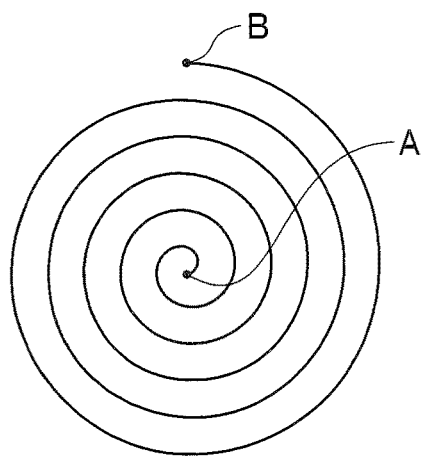
FIG. 11 is a diagram showing an example of a case where, in a scan for acquiring an observed image of an object, the scan is performed so as to advance from the outermost point B to the center point A.

More specifically, the control portion 25 performs control, for example, for causing the end portion of the illumination fiber 12 which includes the distal-end-side end face to swing along a first spiral-shaped track from a center point A toward an outermost point B in FIG. 10 and, after that, causing the end portion to swing along a second spiral-shaped track from the outermost point B toward the center point A in FIG. 11. Further, for example, the control portion 25 adjusts rotation speed and the like of the motors 271A and 272A so that illuminating light emitted via the lens LA is transmitted through the opening portion 271D, and return light emitted via the lens LC is transmitted through the opening portion 272D while causing the end portion of the illumination fiber 12 which includes the distal-end-side end face to swing along the first spiral-shaped track or the second spiral-shaped track. FIG. 10 is a diagram showing an example of a case where, in a scan for acquiring an observed image of an object, the scan is performed so as to advance from the center point A to the outermost point B of the spiral-shaped track. FIG. 11 is a diagram showing an example of a case where, in a scan for acquiring an observed image of an object, the scan is performed so as to advance from the outermost point B to the center point A of the spiral-shaped track.

Figure 12:
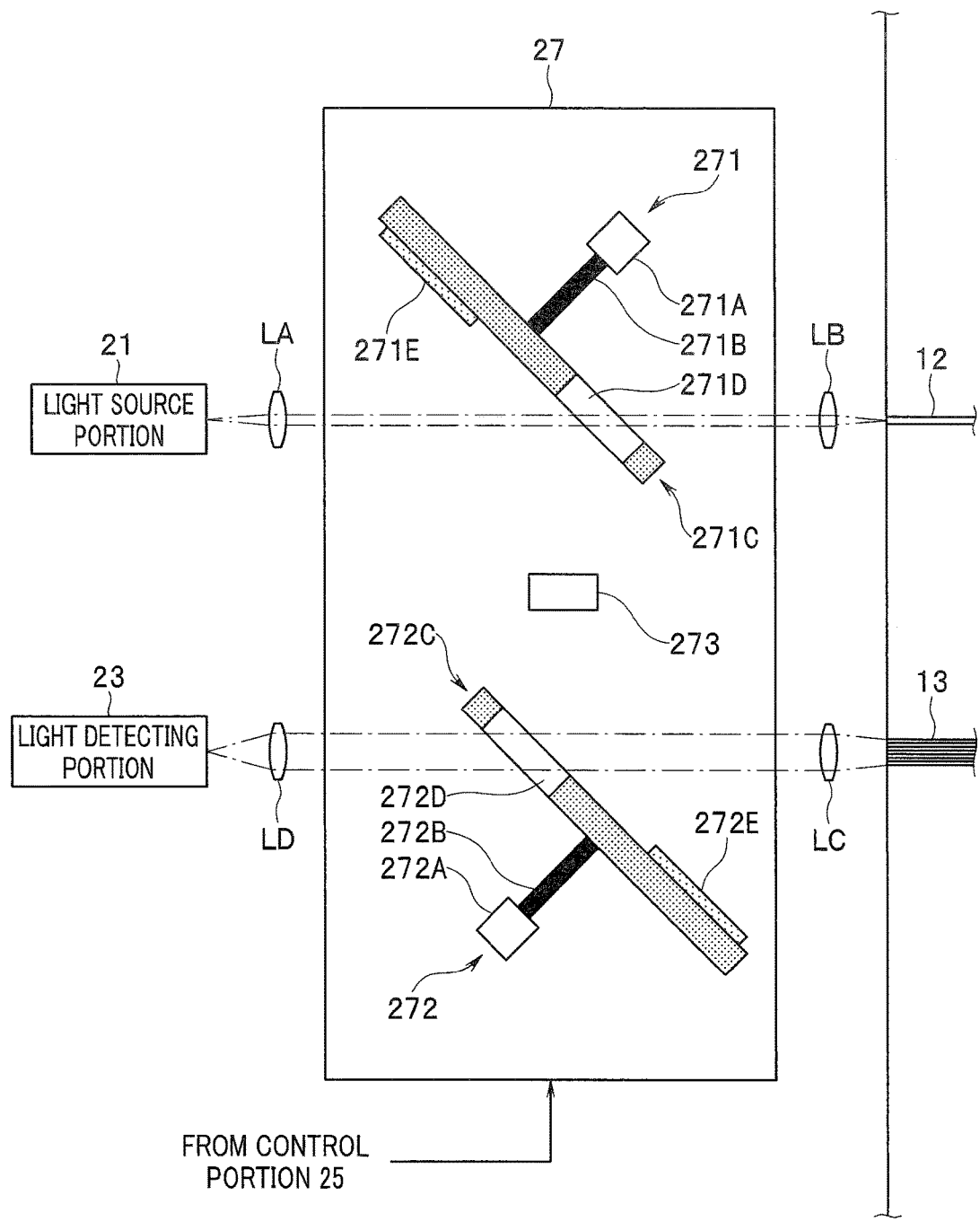
FIG. 12 is a diagram showing an example of an operation state of the optical unit according to the second embodiment.

Then, by the control of the control portion 25 as described above, for example, illuminating light emitted from the light source portion 21 during a period during which the end portion of the illumination fiber 12 which includes the distal-end-side end face is caused to swing along a spiral-shaped track is caused to be incident on the proximal-end-side end face of the illumination fiber 12 after being transmitted through the lens LA, the opening portion 271D and the lens LB sequentially, as shown in FIG. 12. Further, by the control of the control portion 25 as described above, for example, return light emitted from the proximal-end-side end face of the light-receiving fiber group 13 during the period during which the end portion of the illumination fiber 12 which includes the distal-end-side end face is caused to swing along the spiral-shaped track is caused to be incident on the light detecting portion 23 after being transmitted through the lens LC, the opening portion 272D and the lens LD sequentially, as shown in FIG. 12. FIG. 12 is a diagram showing an example of an operation state of the optical unit according to the second embodiment.

The image processing portion 24 generates a first observed image corresponding to one frame using color signals outputted from the light detecting portion 23 during a period during which the illumination fiber 12 is caused to swing along the first spiral-shaped track illustrated in FIG. 10, and outputs the first observed image to the display device 4, based on control of the control portion 25. Further, the image processing portion 24 generates a second observed image corresponding to one frame using color signals outputted from the light detecting portion 23 during a period during which the illumination fiber 12 is caused to swing along the second spiral-shaped track illustrated in FIG. 11, and outputs the second observed image to the display device 4, based on control of the control portion 25.

On the other hand, when detecting that the instruction for causing acquisition of an observed image by the scanning-type endoscope 2 and the body apparatus 3A to be started has been made, the control portion 25 performs control for causing illuminating light supplied from the light source portion 21 to be incident on the proximal-end-side end face of the light-receiving fiber group 13, for the optical unit 27 during the period until the predetermined time period elapses after scanning for acquiring observed images corresponding to a predetermined number of frames is performed.

More specifically, for example, during a period until a predetermined time period PT elapses immediately after scanning for acquiring the first observed image and the second observed image described before is performed, that is, immediately after scanning for acquiring observed images corresponding to two frames is performed, the control portion 25 performs control for causing the end portion of the illumination fiber 12 which includes the distal-end-side end face to stop moving at the center point A, for the scan driving portion 22, and adjusts the rotation speed and the like of the motors 271A and 272A so that the optical path LP is formed.

Figure 13:
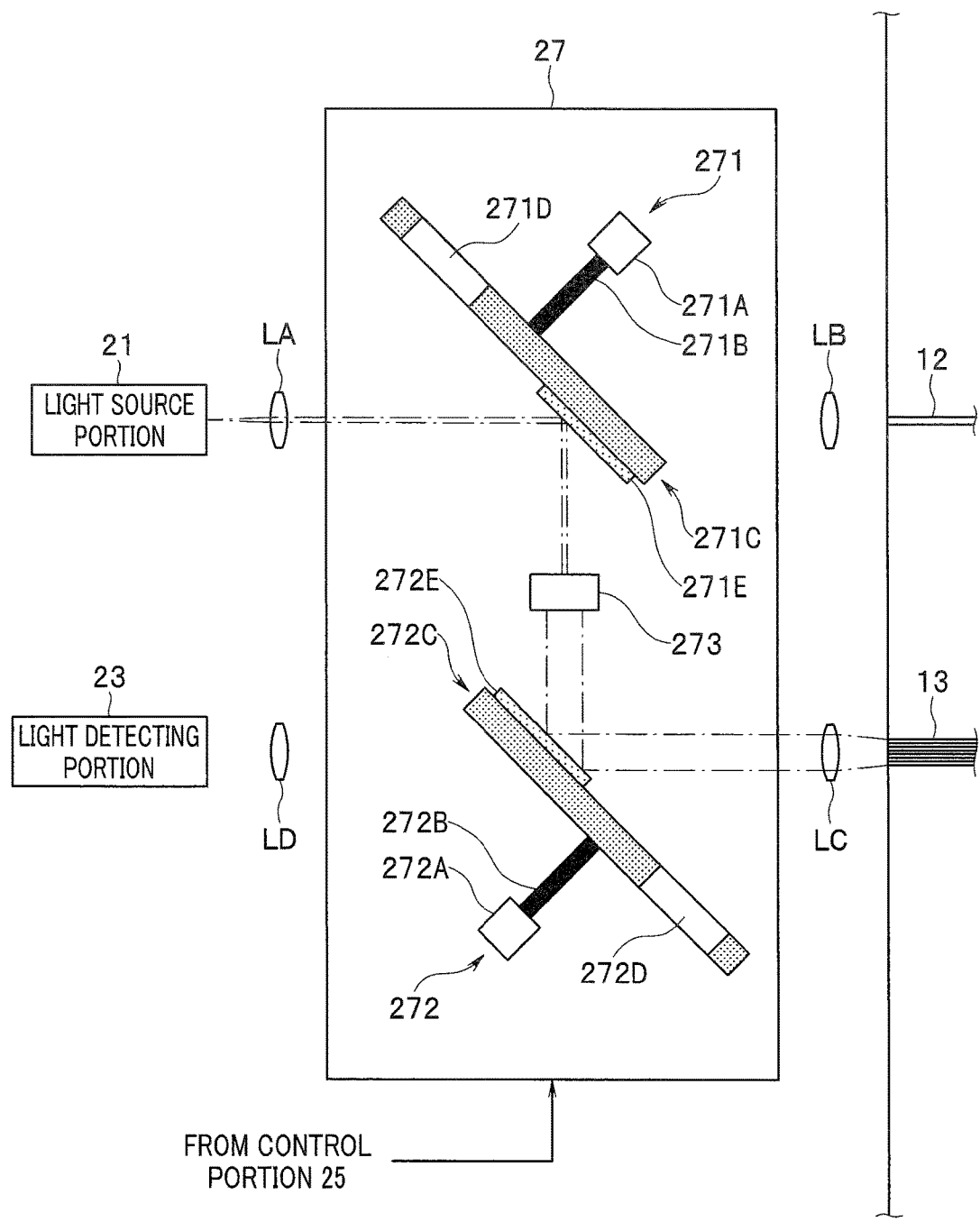
FIG. 13 is a diagram showing an example of the operation state of the optical unit according to the second embodiment different from the example in FIG. 12.

Then, by the control of the control portion 25 as described above, for example, illuminating light emitted from the light source portion 21 during a period of the predetermined time period PT (a period during which the end portion of the illumination fiber 12 which includes the distal-end-side end face stops at a center point on a spiral-shaped track) is caused to be incident on the proximal-end-side end face of the light-receiving fiber group 13 after being transmitted through the lens LA, the mirror 271E, the luminous flux diameter changing portion 273, the mirror 272E and the lens LC sequentially, as shown in FIG. 13. FIG. 13 is a diagram showing an example of an operation state of the optical unit according to the second embodiment.

The image processing portion 24 stops an operation related to generation and output of an observed image during the period of the predetermined time period PT based on control of the control portion 25.

As described above, by the endoscope system 1A according to the present embodiment, it is possible to accelerate recovery of transmittance of the light-receiving fiber group 13 without providing a dedicated optical member and the like in the insertion portion 11. Therefore, according to the present embodiment, it is possible to accelerate recovery of transmittance of a light-receiving fiber without uselessly increasing a diameter of the insertion portion.

Further, as described above, by the endoscope system 1A according to the present embodiment, it is possible to cause illuminating light emitted from the light source portion 21 during the period of the predetermined time period PT which does not contribute to acquisition of an observed image to be incident on the light-receiving fiber group 13. Therefore, by the endoscope system 1A according to the present embodiment, it is possible to accelerate recovery of transmittance of the light-receiving fiber group 13 without interfering with generation of an observed image by the image processing portion 24.

Third Embodiment

FIGS. 14 to 17 relate to a third embodiment of the present invention.

Figure 14:
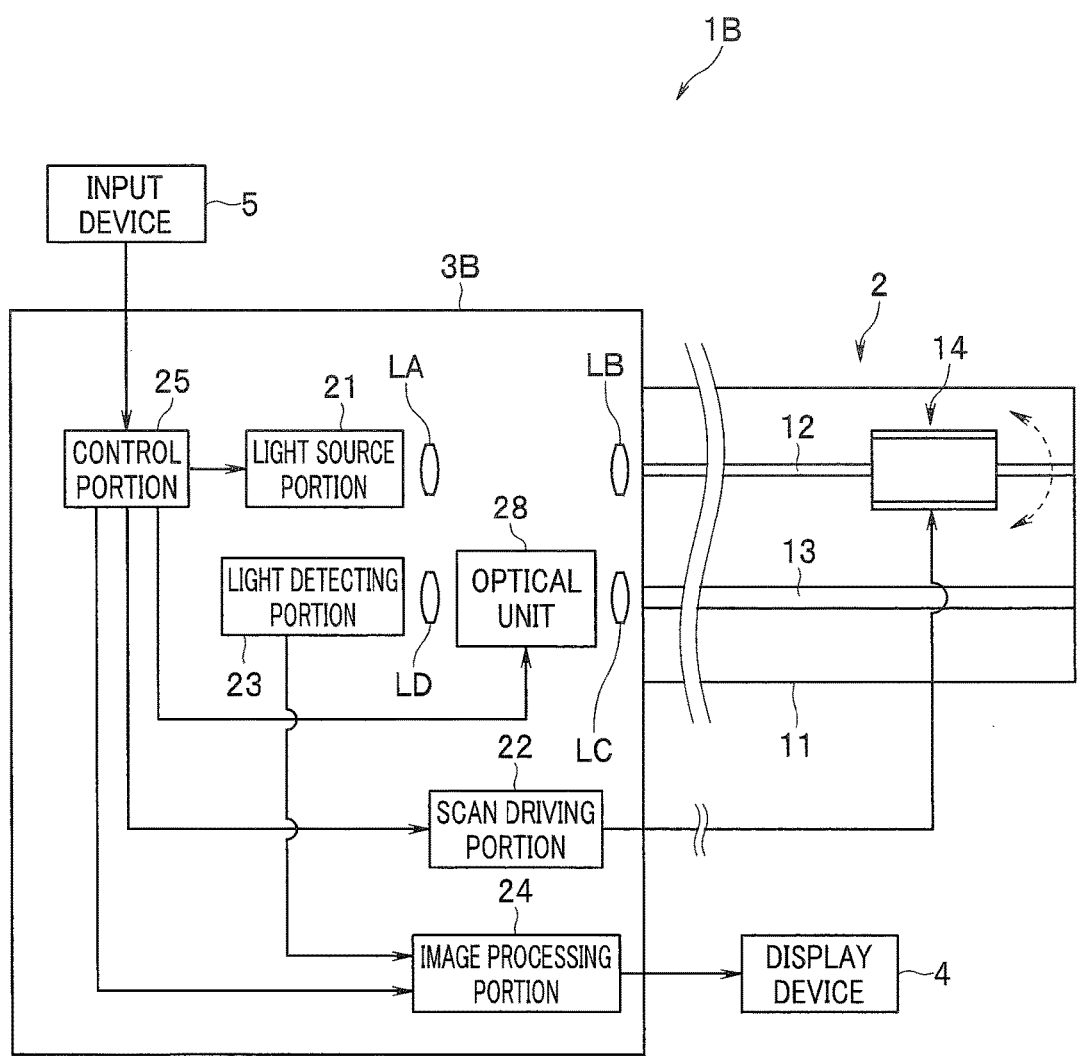
FIG. 14 is a diagram showing a configuration of main portions of an endoscope system according to a third embodiment.

Note that, in the present embodiment, detailed description on parts having configurations and the like similar to those of either the first or second embodiments will be omitted, and description will be made mainly on parts having configurations and the like different from those of both of the first and second embodiments. FIG. 14 is a diagram showing a configuration of main portions of an endoscope system according to the third embodiment.

An endoscope system 1B is configured, for example, having a body apparatus 3B instead of the body apparatus 3 in the endoscope system 1, as shown in FIG. 14. Further, the body apparatus 3B is configured having an optical unit 28 instead of the optical unit 26 in the body apparatus 3.

Figure 15:
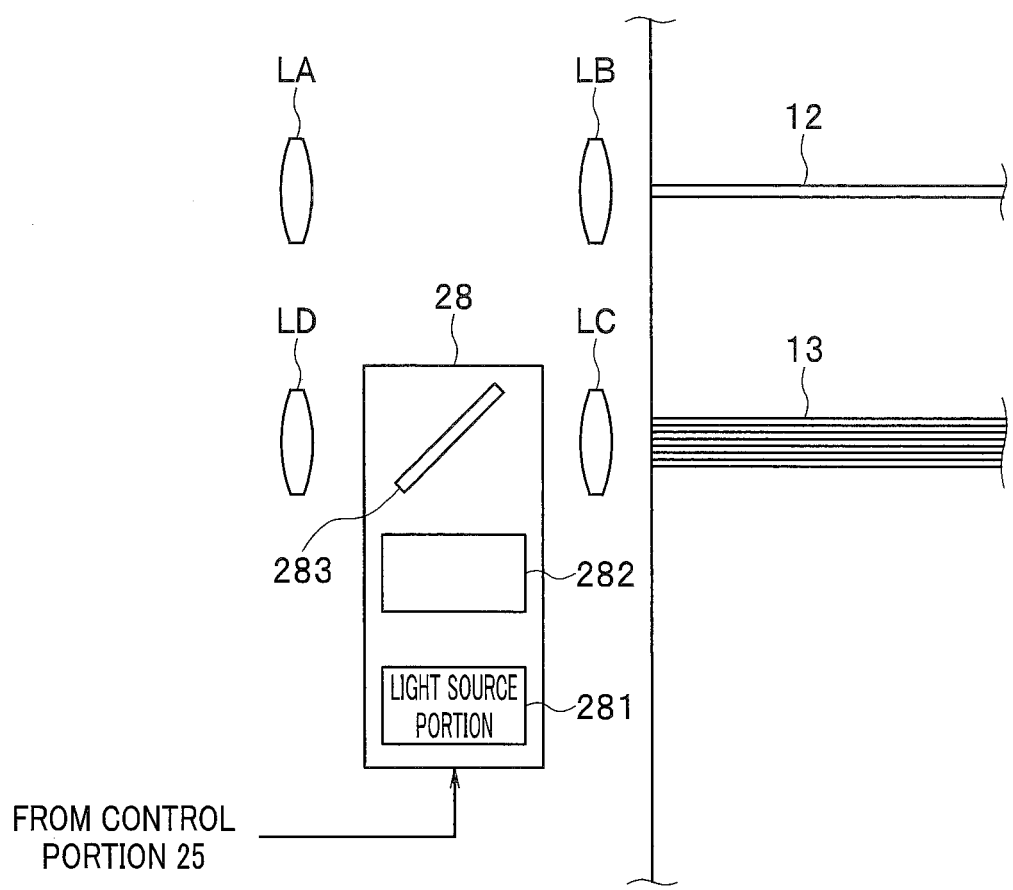
FIG. 15 is a diagram for illustrating an example of a configuration of an optical unit according to the third embodiment.

The optical unit 28 is configured, for example, having a light source portion 281, a luminous flux diameter changing portion 282 and a dichroic mirror 283 as shown in FIG. 15. FIG. 15 is a diagram for illustrating an example of a configuration of the optical unit according to the third embodiment.

The light source portion 281 is configured to be capable of supplying predetermined light provided with a wavelength band which does not overlap with a wavelength band of illuminating light emitted from the light source portion 21 (hereinafter, also referred to as recovery accelerating light) to the luminous flux diameter changing portion 282. Further, the light source portion 281 is configured to be capable of starting or stopping supply of the recovery accelerating light in response to control of the control portion 25.

The luminous flux diameter changing portion 282 is arranged at a predetermined position on an optical path from the light source portion 281 to the dichroic mirror 283. Further, the luminous flux diameter changing portion 282 is provided, for example, with a beam expander and is configured to change a luminous flux diameter of recovery accelerating light emitted from the light source portion 281 so that the luminous flux diameter becomes a size matching a bundle diameter of the light-receiving fiber group 13 (for example, to expand the luminous flux diameter so that the luminous flux diameter becomes a same or substantially same size as the bundle diameter of the light-receiving fiber group 13) and emit the illuminating light to a dichroic mirror 283 side.

The dichroic mirror 283 is configured, for example, being provided with an optical characteristic capable of reflecting recovery accelerating light emitted via the luminous flux diameter changing portion 282 to a lens LC side and causing return light emitted via the lens LC to be transmitted to a lens LD side.

That is, the optical unit 28 can cause recovery accelerating light supplied from the light source portion 281 to be incident on the emission-end-side end face of the light-receiving fiber group 13 by causing the light source portion 281 to operate in response to control of the control portion 25.

The lens LC of the present embodiment is configured, for example, being provided with an optical characteristic of emitting return light emitted from the proximal-end-side end face of the light-receiving fiber group 13 as parallel light, and condensing recovery accelerating light supplied from the optical unit 28 and causing the recovery accelerating light to be incident on the proximal-end-side end face of the light-receiving fiber group 13.

Next, an operation of the endoscope system 1B according to the present embodiment will be described.

The user makes an instruction for causing acquisition of an observed image by the scanning-type endoscope 2 and the body apparatus 3B to be started, by operating the input device 5 after connecting each portion of the endoscope system 1B and turning on power.

When detecting that the instruction for causing acquisition of an observed image by the scanning-type endoscope 2 and the body apparatus 3B to be started has been made, the control portion 25 performs control for causing supply of illuminating light to be started, for the light source portion 21, performs control for causing supply of recovery accelerating light from the light source portion 281 to be started, for the optical unit 28, and performs control for causing the end portion of the illumination fiber 12 which includes the distal-end-side end face to swing so that an illumination position of illuminating light emitted from the insertion portion 11 draws a spiral-shaped track, for the scan driving portion 22.

Figure 16:
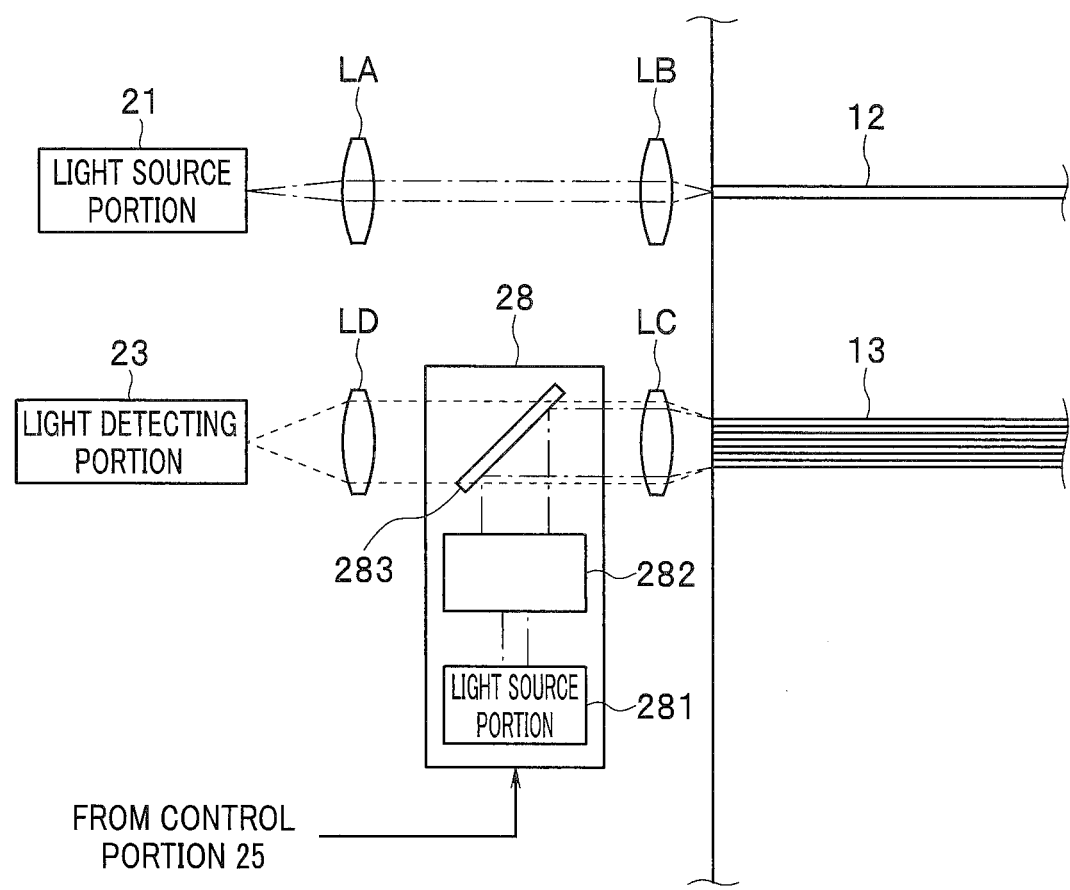
FIG. 16 is a diagram showing an example of an operation state of the optical unit according to the third embodiment.

Then, by the control of the control portion 25 as described above, for example, illuminating light emitted from the light source portion 21 is caused to be incident on the proximal-end-side end face of the illumination fiber 12 after being transmitted through the lens LA and the lens LB sequentially, as shown in FIG. 16. Further, by the control of the control portion 25 as described above, for example, at a same time when return light emitted from the proximal-end-side end face of the light-receiving fiber group 13 is caused to be incident on the light detecting portion 23 via the lens LC, the dichroic mirror 283 and the lens LD, recovery accelerating light reflected by the dichroic mirror 283 is caused to be incident on the proximal-end-side end face of the light-receiving fiber group 13 via the lens LC, as shown in FIG. 16. FIG. 16 is a diagram showing an example of an operation state of the optical unit according to the third embodiment.

Figure 17:
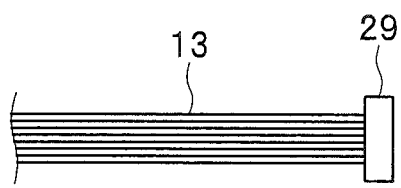
FIG. 17 is a diagram showing an example of a setup position of a filter which can be used together with the optical unit according to the third embodiment.

Note that, in the present embodiment, for example, an optical filter 29 configured to intercept a wavelength band component of recovery accelerating light caused to be incident from the proximal-end-side end face of the light-receiving fiber group 13 may be provided on the distal-end-side end face of the light-receiving fiber group 13 so that the recovery accelerating light caused to be incident on the light-receiving fiber group 13 via the lens LD is not emitted to an outside of the insertion portion 11 (an object illuminated by illuminating light emitted from the illumination fiber 12), as shown in FIG. 17. FIG. 17 is a diagram showing an example of a setup position of the filter which can be used together with the optical unit according to the third embodiment.

As described above, by the endoscope system 1B according to the present embodiment, it is possible to accelerate recovery of transmittance of the light-receiving fiber group 13 without providing a dedicated optical member and the like in the insertion portion 11. Therefore, according to the present embodiment, it is possible to accelerate recovery of transmittance of a light-receiving fiber without uselessly increasing a diameter of an insertion portion.

Further, as described above, by the endoscope system 1B according to the present embodiment, it is possible to cause return light emitted from the light-receiving fiber group 13 to be incident on the light detecting portion 23 while causing recovery accelerating light emitted from the optical unit 28 to be incident on the light-receiving fiber group 13. Therefore, by the endoscope system 1B according to the present embodiment, it is possible to accelerate recovery of transmittance of the light-receiving fiber group 13 without discontinuing display of an observed image on the display device 4.

Note that the present invention is not limited to each embodiment described above, and it is, of course, possible to make various changes and applications within a range not departing from the spirit of the invention.

What is claimed is:

1. An endoscope system comprising:
   an elongated insertion portion insertable into a body cavity of a subject;
   an illumination fiber provided in the insertion portion, the illumination fiber guiding light caused to be incident on a proximal-end-side end face of the insertion portion to a distal-end-side end face of the insertion portion;
   a light-receiving fiber group provided in the insertion portion, the light-receiving fiber group guiding light from the object caused to be incident on the distal-end-side end face of the insertion portion and emitting the light from the proximal-end-side end face of the insertion portion;
   a light source portion generating illuminating light for illuminating an object in the body cavity of the subject, the light source being arranged at a position where the illuminating light is caused to be incident on a proximal-end-side end face of the illumination fiber;
   a light detecting portion arranged at a position where the light from the object emitted from the light-receiving fiber group is caused to be incident;
   a first optical unit arranged on an optical path of the illuminating light generated by the light source portion, the first optical unit being capable of changing the optical path of the illuminating light caused to be incident on the proximal-end-side end face of the illumination fiber;
   a second optical unit arranged on an optical path from the end face of the light-receiving fiber group from which the light from the object is emitted to the light detecting portion, the second optical unit being capable of changing the optical path of the illuminating light changed by the first optical unit to cause the illuminating light to be incident on the end face of the light-receiving fiber group from which the light from the object is emitted; and
   a control portion performing control of whether or not to change the optical path in the first optical unit and the second optical unit.

2. The endoscope system according to claim 1, further comprising:
   an actuator portion provided in the insertion portion and configured to swing a distal-end-side end face of the illumination fiber; and
   a scan driving portion provided outside the insertion portion and configured to supply a drive signal for driving the actuator portion; wherein
   while swinging the distal-end-side end face of the illumination fiber, the control portion causes scanning for acquiring an observed image of the object to be performed, by controlling the first optical unit and the scan driving portion to cause the illuminating light supplied from the light source portion to be incident on the proximal-end-side end face of the illumination fiber, and performs control for causing the illuminating light supplied from the light source portion to be incident on the end face of the light-receiving fiber group from which the light from the object is emitted, for the first optical unit and the second optical unit, during a period until a predetermined time period elapses after scanning for acquiring observed images of the object corresponding to a predetermined number of frames is performed.

3. The endoscope system according to claim 1, wherein the light-receiving fiber group is configured with a plurality of optical fibers bundled, the plurality of optical fibers receiving, by distal-end-side end faces, the return light of the illuminating light emitted to the object from the distal-end-side end face of the illumination fiber and guiding the return light; and
   the endoscope system further comprises a luminous flux diameter changing portion configured to change a luminous flux diameter of the illuminating light supplied from the light source portion to match a bundle diameter of the light-receiving fiber group and emit the illuminating light.

4. The endoscope system according to claim 1, wherein the first optical unit is a movable mirror insertable to and retractable from the optical path of the illuminating light generated by the light source portion; and the second optical unit is a movable mirror insertable to and retractable from the optical path from the end face of the light-receiving fiber group from which the light from the object is emitted to the light detecting portion.

\* \* \* \* \*